US00PP36128P2

(12) United States Plant Patent
Mukundan

(10) Patent No.: US PP36,128 P2
(45) Date of Patent: Sep. 17, 2024

(54) ***SCHEFFLERA* PLANT NAMED 'Mukivy'**

(50) Latin Name: *Schefflera arboricola*
Varietal Denomination: Mukivy

(71) Applicant: Parthasarathy Mukundan, Tamil Nadu (IN)

(72) Inventor: Parthasarathy Mukundan, Tamil Nadu (IN)

( * ) Notice: Subject to any disclaimer, the term of this patent is extended or adjusted under 35 U.S.C. 154(b) by 0 days.

(21) Appl. No.: 18/387,362

(22) Filed: Nov. 6, 2023

(51) Int. Cl.
*A01H 6/00* (2018.01)
*A01H 5/12* (2018.01)

(52) U.S. Cl.
USPC ..... Plt./377

(58) Field of Classification Search
USPC ..... Plt./377
CPC ..... A01H 6/00; A01H 5/02; A01H 5/12
See application file for complete search history.

*Primary Examiner* — Keith O. Robinson
(74) *Attorney, Agent, or Firm* — C. Anne Whealy

(57) ABSTRACT

A new and distinct cultivar of Schefflera plant named 'Mukivy', characterized by its upright and outwardly branching plant habit; relatively vigorous growth habit and rapid growth rate; variegated leaves that are dark green and pale yellow in color; and good interiorscape performance.

3 Drawing Sheets

Figure 1:
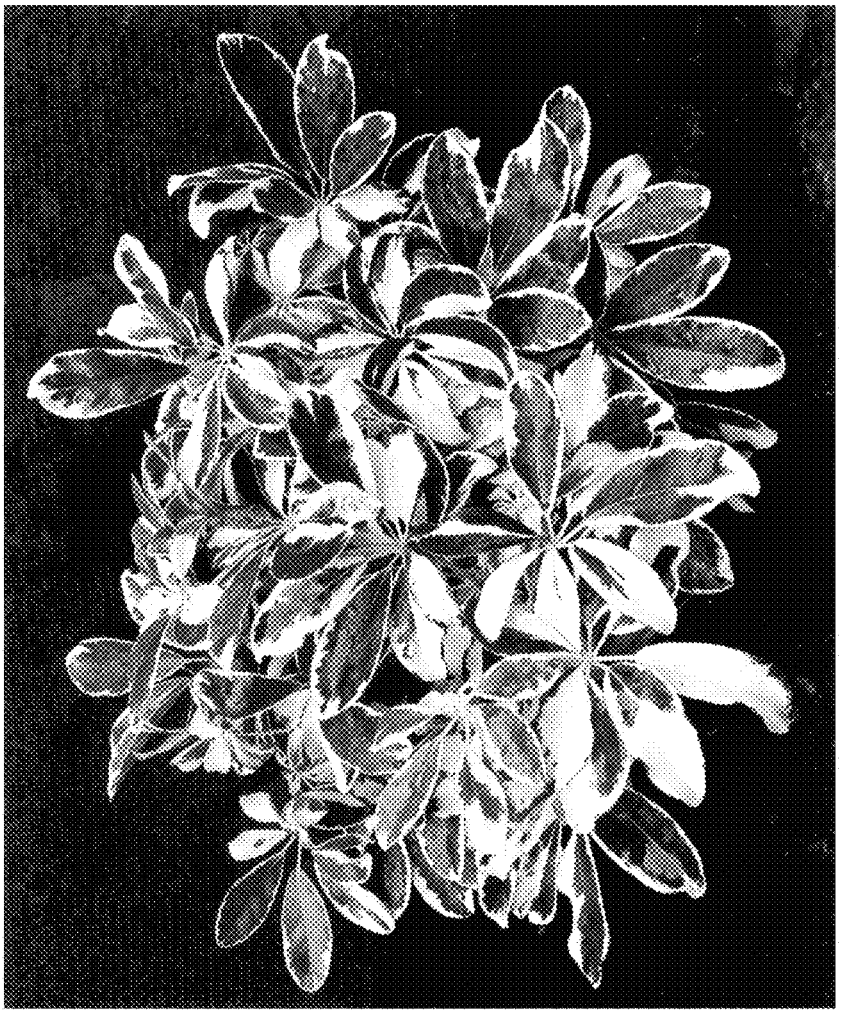

Botanical designation: *Schefflera arboricola.*
Cultivar denomination: 'MUKIVY'.

STATEMENT REGARDING PRIOR DISCLOSURES BY INVENTOR/APPLICANT

The Inventor/Applicant asserts that no sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosures prior to the filing date but less than one year prior to the effective filing date.

BACKGROUND OF THE INVENTION

The present invention relates to a new and distinct cultivar of Schefflera plant, botanically known as *Schefflera arboricola* and hereinafter referred to by the cultivar name 'Mukivy'.

The new Schefflera plant is a product of a controlled breeding program conducted by the Inventor at Illalore Farm, Chennai, India. The objective of the breeding program is to create new strong and vigorous Schefflera plants with unique leaf variegation patterns and good postproduction longevity.

The new Schefflera plant is a naturally-occurring branch mutation of an unnamed non-variegated selection of *Schefflera arboricola*, not patented. The new Schefflera plant was discovered and selected by the Inventor on a single plant from within a population of plants of the mutation parent in a controlled environment at Illalore Farm, Chennai, India in September, 2013.

Asexual reproduction of the new Schefflera plant by terminal and stem cuttings in a controlled environment at Illalore Farm, Chennai, India since December, 2013 has shown that the unique features of this new Schefflera plant are stable and reproduced true to type in successive generations of asexual reproduction.

SUMMARY OF THE INVENTION

Plants of the new Schefflera have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mukivy'. These characteristics in combination distinguish 'Mukivy' as a new and distinct Schefflera plant:

1. Upright and outwardly branching plant habit.
2. Relatively vigorous growth habit and rapid growth rate.
3. Variegated leaves that are dark green and pale yellow in color.
4. Good interiorscape performance.

Plants of the new Schefflera differ primarily from plants of the mutation parent selection in leaflet color as plants of the new Schefflera have dark green and pale yellow-colored leaflets whereas plants of the mutation parent selection have non-variegated dark green-colored leaves. In addition, developing stems of plants of the new Schefflera are medium green in color with random creamy white-colored streaks whereas stems of plants of the mutation parent selection have solid pale green-colored stems without any streaks.

Plants of the new Schefflera can also be compared to plants of *Schefflera arboricola* 'OSV002', disclosed in U.S. Plant Pat. No. 32,734. In side-by-side comparisons, plants of the new Schefflera differ from plants of 'OSV002' in the following characteristics:

1. Stems of plants of the new Schefflera are medium green in color with random pale yellow-colored streaks whereas stems of plants of 'OSV002' are solid medium green in color without any streaks.

2. Leaves of plants of the new Schefflera are more undulate and rugose than leaves of plants of 'OSV002'.
3. Leaves of plants of the new Schefflera are dark green and pale yellow variegated whereas leaves of plants of 'OSV002' are green and yellow-green variegated.

BRIEF DESCRIPTION OF THE PHOTOGRAPHS

The accompanying photographs illustrate the overall appearance of the new Schefflera plant showing the colors as true as it is reasonably possible to obtain in colored reproductions of this type. Colors in the photographs may differ slightly from the color values cited in the detailed botanical description which accurately describe the colors of the new Schefflera plant.

The photograph on the first sheet (FIG. 1) is a side perspective view of a typical plant of 'Mukivy' grown in a container.

Figure 2:
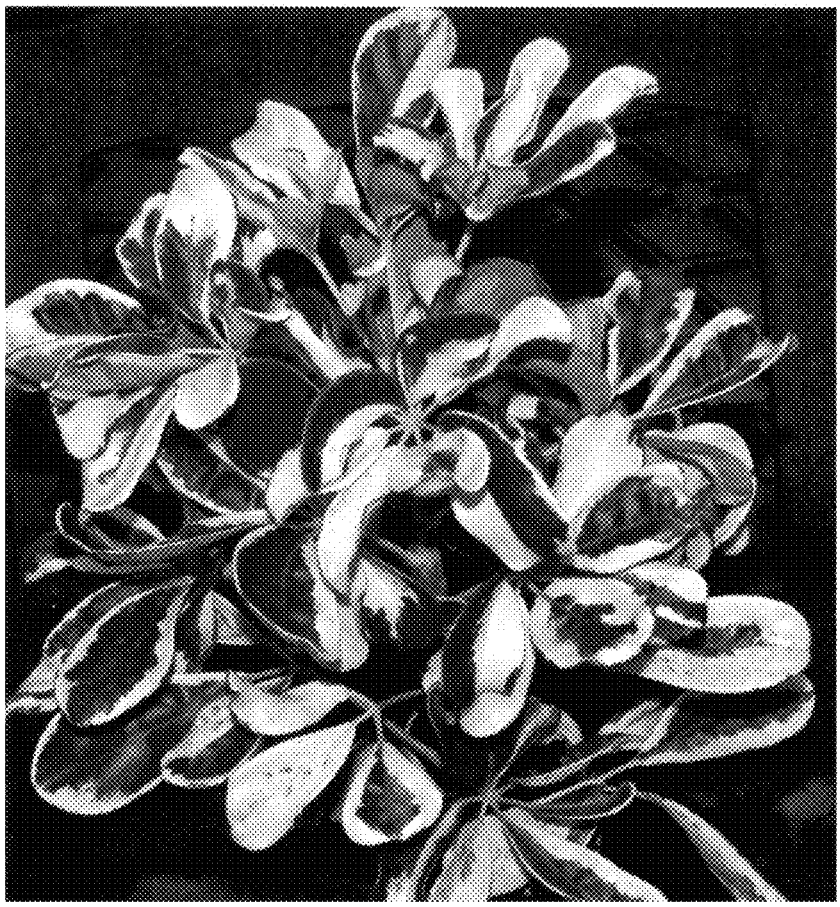

The photograph on the second sheet (FIG. 2) is a close-up view of a typical plant of 'Mukivy'.

Figure 3:
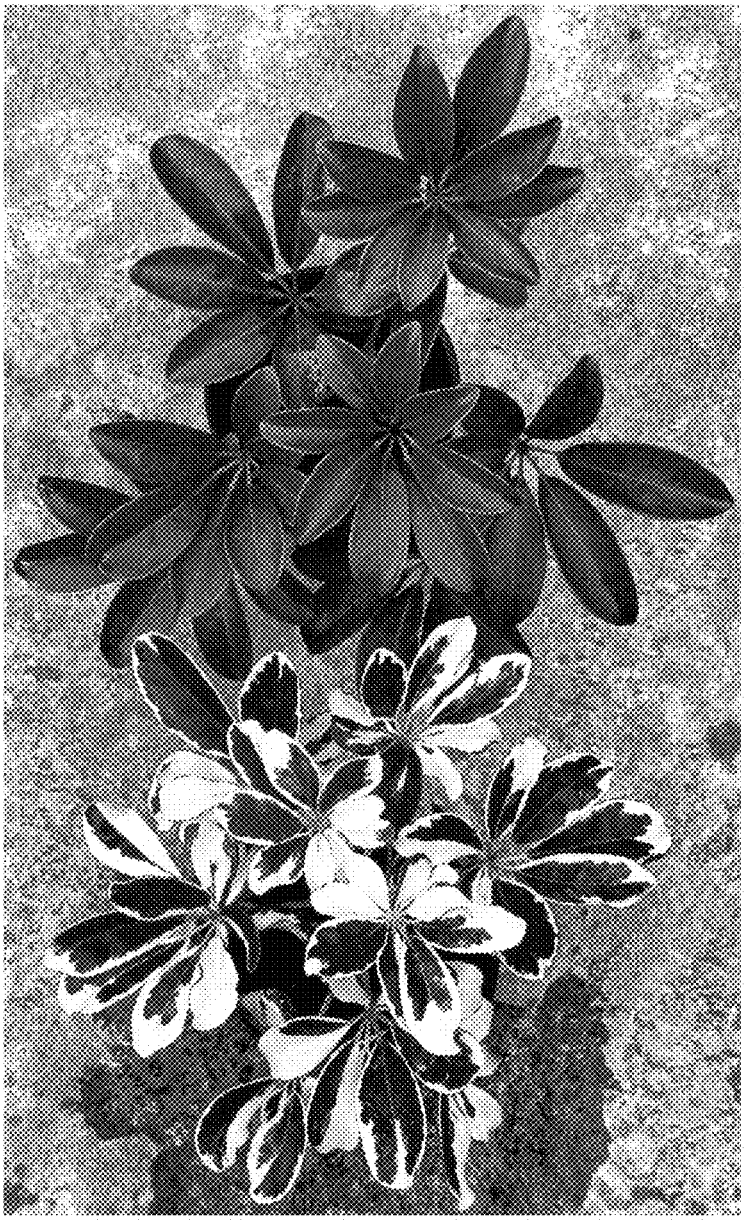

The photograph on the third sheet (FIG. 3) is a top perspective view of a typical plant of 'Mukivy' (left) and its mutation parent, the unnamed selection of *Schefflera arboricola* (right).

DETAILED BOTANICAL DESCRIPTION

The aforementioned photographs and following observations and measurements describe plants grown in 15-cm containers during the spring and early summer in a polyethylene-covered greenhouse in Miami, Florida. Plants were grown under environmental conditions and cultural practices which approximate those generally used in commercial Schefflera production. During the production of the plants, day temperatures ranged from 25C to 32C and night temperatures ranged from 15C to 23C and were grown under 80% shade. Plants were one year old when the photographs and the detailed description were taken. In the following description, color references are made to The Royal Horticultural Society Colour Chart, 2015 Edition, except where general terms of ordinary dictionary significance are used.

BOTANICAL CLASSIFICATION:

*Schefflera arboricola* 'Mukivy'.

PARENTAGE:

Naturally-occurring branch mutation of an unnamed selection of *Schefflera arboricola*, not patented.

PROPAGATION:

*Type*.—By terminal and stem cuttings.

*Time to initiate roots, summer*.—About 30 days at temperatures about 20C to 25C.

*Time to initiate roots, winter*.—About 45 days at temperatures about 18C to 20C.

*Time to produce a rooted young plant, summer*.—About six to eight weeks at temperatures about 36C.

*Time to produce a rooted young plant, winter*.—About eight to ten weeks at temperatures about 25C.

*Root description*.—Medium in thickness, fibrous; typically off-white in color, actual color of the roots is dependent on substrate composition, water quality, fertilizer type and formulation, substrate temperature and physiological age of roots.

*Rooting habit*.—Freely branching; dense.

PLANT DESCRIPTION:

*Plant and growth habit*.—Upright and outwardly branching plant habit; relatively vigorous growth habit and rapid growth rate; freely branching habit with lateral branches potentially forming at every node.

*Plant height*.—About 27 cm.

*Plant diameter or spread*.—About 28 cm.

*Stem description*.—Lateral branch length: About 15 cm. Lateral branch diameter: About 9 mm. Internode length: About 1.5 cm to 5 cm. Aspect: Mostly upright to outwardly, about 45 degrees from vertical. Strength: Strong, somewhat flexible. Texture and luster: Smooth, glabrous; matte. Color, developing: Closest to 144A with random vertical streaks, closest to 10D. Color, developed: Closest to 198B; moderately covered with circular lenticels, closest to 199A in color.

*Leaf description*.—Arrangement: Alternate; leaves compound with six to seven leaflets per leaf. Leaf length: About 4.7 cm. Leaf width: About 8.7 cm. Leaflet length: About 3 cm. Leaflet width: About 2 cm. Leaflet shape: Oblanceolate. Leaflet apex: Obtuse. Leaflet base: Attenuate. Leaflet margin: Entire to irregular, but not lobed; moderately undulate. Leaflet texture and luster, upper surface: Rugose and randomly puckered, glabrous; moderately glossy. Leaflet texture and luster, lower surface: Rugose and randomly puckered, glabrous; matte. Leaflet venation pattern: Pinnate. Leaflet color: Developing and fully expanded leaflets, upper surface: Dark green-colored sectors (mostly central), closest to between 147A and N189A; pale yellow-colored sectors (mostly marginal), closest to 10D; venation, similar to lamina colors. Developing and fully expanded leaflets, lower surface: Medium green-colored sectors (mostly central), closest to 138A; yellowish green-colored sectors (mostly marginal), closest to 154B to 154D; venation, similar to lamina colors. Leaf petioles: Length: About 3.1 cm. Diameter: About 2.5 mm by 3 mm. Strength: Strong, flexible. Aspect: About 45 degrees from lateral branch axis. Texture and luster, upper and lower surfaces: Smooth, glabrous; slightly glossy. Color, upper and lower surfaces: Closest to 144A to 144B. Leaflet petioles: Length: About 7 mm. Diameter: About 1.5 mm. Strength: Strong, flexible. Aspect: About 30 to 45 degrees from leaf petiole axis. Texture and luster, upper surface: Smooth, glabrous; moderately glossy. Texture and luster, lower surface: Smooth, glabrous; matte. Color, upper and lower surfaces: Closest to 144A to 144B.

FLOWER DESCRIPTION:

To date, flower initiation and development have not been observed on plants of the new Schefflera.

PATHOGEN & PEST RESISTANCE:

To date, plants of the new Schefflera have not been observed to be resistant to pathogens or pests common to Schefflera plants.

TEMPERATURE TOLERANCE:

Plants of the new Schefflera have been observed to be tolerant to temperatures ranging from about 8 C to about 40 C and to be suitable for USDA Hardiness Zones 10 to 13.

It is claimed:

1. A new and distinct Schefflera plant named 'Mukivy' as illustrated and described.

* * * * *